(12) United States Patent
Wang et al.

(10) Patent No.: US 11,589,834 B2
(45) Date of Patent: Feb. 28, 2023

(54) DEEP NEURAL NETWORK FOR CT METAL ARTIFACT REDUCTION

(71) Applicant: RENSSELAER POLYTECHNIC INSTITUTE, Troy, NY (US)

(72) Inventors: Ge Wang, Loudonville, NY (US); Lars Arne Gjesteby, Cohasset, MA (US); Qingsong Yang, Troy, NY (US); Hongming Shan, Troy, NY (US)

(73) Assignee: Rensselaer Polytechnic Institute, Troy, NY (US)

(*) Notice: Subject to any disclaimer, the term of this patent is extended or adjusted under 35 U.S.C. 154(b) by 109 days.

(21) Appl. No.: 16/978,258

(22) PCT Filed: Mar. 6, 2019

(86) PCT No.: PCT/US2019/020916
§ 371 (c)(1),
(2) Date: Sep. 4, 2020

(87) PCT Pub. No.: WO2019/173452
PCT Pub. Date: Sep. 12, 2019

(65) Prior Publication Data
US 2021/0000438 A1    Jan. 7, 2021

Related U.S. Application Data

(60) Provisional application No. 62/813,972, filed on Mar. 5, 2019, provisional application No. 62/661,323, filed
(Continued)

(51) Int. Cl.
*A61B 6/00* (2006.01)
*A61B 6/03* (2006.01)
(Continued)

(52) U.S. Cl.
CPC ............ *A61B 6/5258* (2013.01); *A61B 6/032* (2013.01); *A61B 6/5205* (2013.01); *G06N 3/084* (2013.01);
(Continued)

(58) Field of Classification Search
CPC ...... G06N 3/084; G06N 5/046; G06T 7/0012; G06T 11/008; G06T 2207/20084; A61B 6/5258; A61B 6/032; A61B 6/5205
See application file for complete search history.

(56) References Cited

U.S. PATENT DOCUMENTS

2008/0253521 A1    10/2008    Boyden et al.
2016/0364856 A1*   12/2016    Zheng .................... A61B 6/032
(Continued)

FOREIGN PATENT DOCUMENTS

WO    2017223560 A1    12/2017

OTHER PUBLICATIONS

Meyer et al., "Frequency split metal artifact reduction (FSMAR) in computed tomography", Medical Physics, 39(4), pp. 1904-1916, Apr. 2012 (Year: 2012).*
(Continued)

*Primary Examiner* — Vu Le
*Assistant Examiner* — Julius Chai
(74) *Attorney, Agent, or Firm* — Murtha Cullina LLP; Anthony P. Gangemi

(57) ABSTRACT

A deep neural network for metal artifact reduction is described. A method for computed tomography (CT) metal artifact reduction (MAR) includes generating, by a projection completion circuitry, an intermediate CT image data based, at least in part, on input CT projection data. The intermediate CT image data is configured to include relatively fewer artifacts than an uncorrected CT image reconstructed from the input CT projection data. The method
(Continued)

further includes generating, by an artificial neural network (ANN), CT output image data based, at least in part, on the intermediate CT image data. The CT output image data is configured to include relatively fewer artifacts compared to the intermediate CT image data. The method may further include generating, by detail image circuitry, detail CT image data based, at least in part, on input CT image data. The CT output image data is generated based, at least in part, on the detail CT image data.

12 Claims, 5 Drawing Sheets

Related U.S. Application Data on Apr. 23, 2018, provisional application No. 62/639,887, filed on Mar. 7, 2018.

(51) Int. Cl.

| | |
|---|---|
| *G06N 3/08* | (2006.01) |
| *G06N 5/04* | (2006.01) |
| *G06T 11/00* | (2006.01) |
| *G06T 7/00* | (2017.01) |
| *G06N 3/084* | (2023.01) |
| *G06N 5/046* | (2023.01) |

(52) U.S. Cl.
CPC ............ *G06N 5/046* (2013.01); *G06T 7/0012* (2013.01); *G06T 11/008* (2013.01); *G06T 2207/20084* (2013.01)

(56) References Cited

U.S. PATENT DOCUMENTS

| | | | |
|---|---|---|---|
| 2018/0350113 A1* | 12/2018 | Goto | A61B 6/5258 |
| 2019/0108441 A1* | 4/2019 | Thibault | G06N 20/00 |
| 2019/0108904 A1* | 4/2019 | Zhou | G06N 3/08 |
| 2019/0328348 A1* | 10/2019 | De Man | G16H 30/40 |
| 2021/0056688 A1* | 2/2021 | Xu | G06T 7/0012 |

OTHER PUBLICATIONS

Lee et al., "Deep-Neural-Network-Based Sinogram Synthesis for Sparse-View CT Image Reconstruction," IEEE Transaction on Radiation and Plasma Medical Sciences, vol. 3, No. 2, pp. 109-119, Mar. 2018 (Year: 2018).*

Meyer et al., "Normalized metal artifact reduction (NMAR) in computed tomography", Medical Physics, vol. 37, No. 10, Oct. 2010 (Year: 2010).*

International Search Report and The Written Opinion of the International Searching Authority, International Application No. PCT/US2019/020916, dated May 15, 2019.

Gjesteby, L., et al., "Deep Learning Methods for CT Image-Domain Metal Artifact Reduction," Proceedings vol. 10391, Developments in X-Ray Tomography XI, pp. 1-7, Sep. 25, 2017.

\* cited by examiner

DEEP NEURAL NETWORK FOR CT METAL ARTIFACT REDUCTION

CROSS REFERENCE TO RELATED APPLICATION(S)

This application claims the benefit of U.S. Provisional Application No. 62/639,887, filed Mar. 7, 2018, U.S. Provisional Application No. 62/661,323, filed Apr. 23, 2018, and U.S. Provisional Application No. 62/813,972, filed Mar. 5, 2019, and which are incorporated by reference as if disclosed herein in their entireties.

FIELD

The present disclosure relates to metal artifact reduction (MAR), in particular to, a deep neural network for CT (computed tomography) metal artifact reduction.

BACKGROUND

Artifacts resulting from features, e.g., metal objects, have been a persistent problem in CT (computed tomography) images over the last four decades. One approach to overcome the effects of the metal objects is to replace corrupt projection data with values synthesized from an interpolation scheme. Another approach includes reprojection of a prior image. Existing correction methods, including for example, an interpolation- and normalization-based technique ("NMAR"), may not produce satisfactory results for some clinical applications. Residual image artifacts may remain in challenging cases and, in some instances, new artifacts can be introduced by the interpolation scheme itself. Thus, artifacts, e.g., metal artifacts, continue to be a major impediment, particularly in radiation and proton therapy planning as well as in orthopedic imaging.

Currently, artifacts, e.g., metal artifacts, in CT images continue to hinder clinical diagnosis. Although a number of artifact reduction techniques have been implemented over the past several years, challenges remain and sufficient image quality may not always be achieved. For example, radiation and proton therapy planning are particularly sensitive to errors in the CT images, since incorrect estimation of a treatment beam stopping power may result in under treatment and tumor recurrence or unnecessary radiation to the surrounding healthy tissues.

SUMMARY

In some embodiments, a method for computed tomography (CT) metal artifact reduction (MAR) is provided. The method includes generating, by a projection completion circuitry, an intermediate CT image data based, at least in part, on input CT projection data. The intermediate CT image data is configured to include relatively fewer artifacts than an uncorrected CT image reconstructed from the input CT projection data. The method further includes generating, by an artificial neural network (ANN), CT output image data based, at least in part, on the intermediate CT image data. The CT output image data is configured to include relatively fewer artifacts compared to the intermediate CT image data.

In some embodiments of the method, the method further includes generating, by detail image circuitry, detail CT image data based, at least in part, on input CT image data. The CT output image data is generated based, at least in part, on the detail CT image data.

In some embodiments of the method, the ANN is trained based, at least in part, on a mean squared error loss function. In some embodiments of the method, the ANN is trained based, at least in part, on a perceptual loss function. In some embodiments of the method, generating the intermediate CT image data includes interpolation and normalization with prior CT projection data. In some embodiments of the method, the ANN is a convolutional neural network (CNN).

In some embodiments of the method, the ANN includes a sequence of convolution stages and a sequence of deconvolution stages. Each convolution stage includes a convolution layer and a rectified linear unit and each deconvolution stage includes a deconvolution layer and a rectified linear unit.

In some embodiments of the method, the ANN includes an intermediate stream, a detail stream and an output stream. The intermediate stream and the detail stream each include an initial convolution stage and a sequence of residual units. The output stream includes a sequence of convolution stages and an output stage. Each convolution stage includes a convolution layer, a batch normalization layer and a rectified linear unit. The output stage includes a convolution layer and a rectified linear unit. In some embodiments of the method, each residual unit includes a sequence of a first convolution stage, a second convolution stage and a combiner stage. The combiner stage is configured to receive an input to the residual unit and an output of the second convolution stage. An output of the residual unit corresponds to an output of the combiner stage.

In some embodiments, an apparatus for computed tomography (CT) metal artifact reduction (MAR) is provided. The apparatus includes a projection completion circuitry configured to generate an intermediate CT image data based, at least in part, on input CT projection data. The intermediate CT image data is configured to include relatively fewer artifacts than an uncorrected CT image reconstructed from the input CT projection data. The apparatus further includes an artificial neural network (ANN) configured to generate CT output image data based, at least in part, on the intermediate CT image data. The CT output image data is configured to include relatively fewer artifacts compared to the intermediate CT image data.

In some embodiments, the apparatus may further include detail image circuitry configured to generate detail CT image data based, at least in part, on input CT image data. The CT output image data is generated based, at least in part, on the detail CT image data.

In some embodiments of the apparatus, the ANN is trained based, at least in part, on a mean squared error loss function. In some embodiments of the apparatus, the ANN is trained based, at least in part, on a perceptual loss function. In some embodiments of the apparatus, generating the intermediate CT image data includes interpolation and normalization with prior CT projection data. In some embodiments of the apparatus, the ANN is a convolutional neural network (CNN).

In some embodiments of the apparatus, the ANN includes a sequence of convolution stages and a sequence of deconvolution stages. Each convolution stage includes a convolution layer and a rectified linear unit and each deconvolution stage includes a deconvolution layer and a rectified linear unit.

In some embodiments of the apparatus, the ANN includes an intermediate stream, a detail stream and an output stream. The intermediate stream and the detail stream each include an initial convolution stage and a sequence of residual units. The output stream includes a sequence of convolution stages and an output stage. Each convolution stage includes a convolution layer, a batch normalization layer and a rectified linear unit and the output stage includes a convolution layer and a rectified linear unit.

In some embodiments of the apparatus, each residual unit includes a sequence of a first convolution stage, a second convolution stage and a combiner stage. The combiner stage is configured to receive an input to the residual unit and an output of the second convolution stage. An output of the residual unit corresponds to an output of the combiner stage.

In some embodiments, a computed tomography (CT) metal artifact reduction (MAR) device is provided. The device includes means to perform any embodiment of the method. In some embodiments, a computer readable storage device is provided. The computer readable storage device has stored thereon instructions that when executed by one or more processors result in the following operations including any embodiment of the method.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Figure 1:
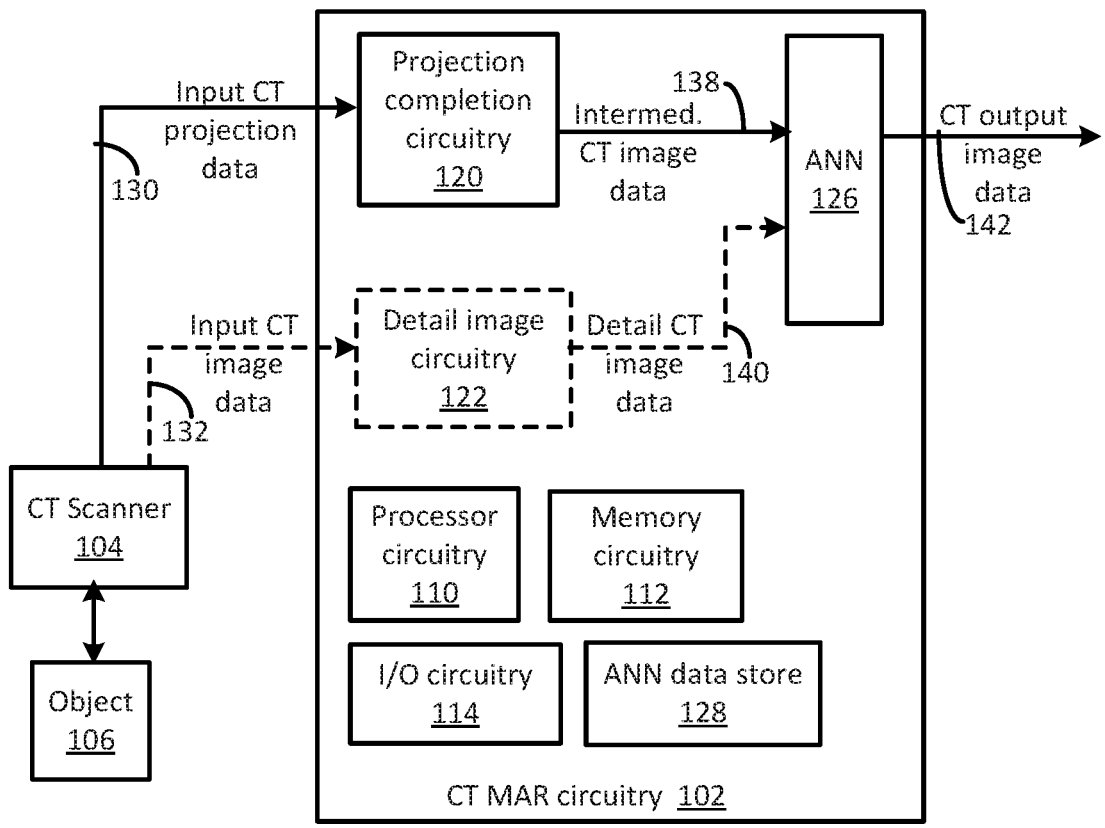
FIG. 1 illustrates a functional block diagram of a system that includes a computed tomography (CT) metal artifact reduction (MAR) device consistent with several embodiments of the present disclosure.

There are a number of classes of artifact reduction (e.g., metal artifact reduction (MAR)) techniques, with projection completion being relatively widely developed. Generally, these techniques are configured to replace corrupt sinogram data in the artifact, e.g., metal, trace with data synthesized by an interpolation technique, reprojection from a prior image or a combination of both that includes normalization. One example technique is normalized metal artifact reduction ("NMAR"). Other classes of artifact reduction methods include scan acquisition improvement, physics-based preprocessing, iterative reconstruction and image postprocessing. While image postprocessing algorithms have had some success, they are more useful when combined with sinogram domain correction. The current clinical techniques may fall short in providing requisite image quality for the most demanding applications, particularly in radiation and proton therapy planning.

Deep learning may provide a solution to the long-standing artifact reduction problem. Deep learning, including for example convolutional neural networks (CNNs), has been successfully applied to medical image processing and analysis tasks. Generally, training a CNN includes providing ground truth artifact-free images that may be used as network labels (i.e., training images). Typically, a ground truth artifact-free image is configured to be identical to an input image except for an artifact present in the input image that the CNN is to be trained to remove.

An artificial neural network (ANN) is a network of elements (e.g., nodes) configured to receive input, change their internal state (activation) according to that input, and produce output depending on the input and activation. The network is formed by connecting the output of selected nodes to the input of other nodes to form a directed, weighted graph. The weights as well as the functions that compute the activation can be modified by learning (e.g., training).

A deep neural network is an ANN that has a plurality of layers between the input and output layers. A relationship between the input and the output may be linear or non-linear. A convolutional neural network (CNN) is a type of deep, feed-forward ANN, that includes one or more convolutional layers with fully connected layers on top. A multilayer perceptron (MLP) is a type of feed-forward ANN that includes at least three layers of nodes and each node, except for the input nodes, uses a nonlinear activation function. An MLP may be trained using back propagation, a supervised learning technique. The multiple layers and non-linear activation of an MLP distinguish it from a linear perceptron. CNNs are a type of deep ANN that use a variation of multilayer perceptrons designed to use minimal preprocessing. As used herein, "ANN" may include, but is not limited to, a CNN, a residual CNN, a generative adversarial network (GAN), etc.

Deep learning is a type of machine learning technique that uses a cascade of a plurality of layers of nonlinear processing units for feature extraction and transformation. Each successive layer uses the output from the previous layer as input. Deep learning techniques learn in supervised (e.g., classification) and/or unsupervised (e.g., pattern analysis) manners. Deep learning algorithms learn multiple levels of representations that correspond to different levels of abstraction. In other words, deep-learning methods are representation-learning methods with multiple levels of representation, obtained by composing simple but non-linear modules that each transform the representation at one level into a representation at a higher, slightly more abstract level. With the composition of enough such transformations, very complex functions can be learned.

Generally, the present disclosure relates to metal artifact reduction (MAR) in computed tomography images. A method and/or apparatus are configured to perform an initial metal artifact reduction using a projection completion technique. Projection completion may be performed on input CT projection data to produce intermediate CT image data. The method and/or apparatus are configured to perform further metal artifact reduction on the intermediate CT image data using an artificial neural network. The combination of projection completion and ANN MAR is configured to provide relatively better MAR than either technique alone.

In an embodiment, a method for computed tomography (CT) metal artifact reduction (MAR) includes generating, by a projection completion circuitry, an intermediate CT image data based, at least in part, on input CT projection data. The intermediate CT image data is configured to include relatively fewer artifacts than an uncorrected CT image reconstructed from the input CT projection data. The method further includes generating, by an artificial neural network (ANN), CT output image data based, at least in part, on the intermediate CT image data. The CT output image data is configured to include relatively fewer artifacts compared to the intermediate CT image data.

In another embodiment, the method further includes generating, by detail image circuitry, detail CT image data based, at least in part, on input CT image data. The CT output image data is generated based, at least in part, on the detail CT image data.

As used herein, "image data" corresponds to pixel values that may be provided to a display, thus, image data corresponds to an image that may be displayed. As further used herein, image data may include image data for an entire image or a portion of an image. A portion of an image may correspond to an image patch.

FIG. 1 illustrates a functional block diagram 100 of a system that includes a computed tomography (CT) metal artifact reduction (MAR) circuitry 102 consistent with several embodiments of the present disclosure. The system 100 may further include a CT scanner 104 configured to generate and provide a plurality of beams of x-ray radiation to an object 106 and to capture (i.e., detect) resulting attenuated and/or scattered x-ray radiation. The CT scanner 104 may be further configured to generate a sinogram corresponding to the detected x-ray radiation and to reconstruct a CT image based, at least in part, on a plurality of sinograms. The object 106 may contain a metal implant, e.g., artificial joint, pin, screw and/or tooth fillings. The metal feature may corrupt one or more sinograms and a CT image reconstructed from the corrupted sinogram(s) may then include metal artifacts.

CT MAR circuitry 102 is configured to receive input CT projection data 130 from, e.g., CT scanner 104. As used herein, the input CT projection data corresponds to an input sinogram. CT MAR circuitry 102 may be further configured to receive input CT image data 132 from, e.g., CT scanner 104. In one embodiment, CT MAR circuitry 102 is configured to generate CT output image data 142 based, at least in part, on input CT projection data 130. In another embodiment, CT MAR circuitry 102 may be configured to generate CT output image data 142 based, at least in part, on input CT projection data 130 and based, at least in part, on input CT image data 132. An output CT image corresponding to the CT output image data 142 is configured to contain fewer artifacts than an uncorrected CT image corresponding to input CT projection data 130 and/or input CT image data 132.

CT MAR circuitry 102 includes processor circuitry 110, memory circuitry 112 and input/output (I/O) circuitry 114. In an embodiment, CT MAR circuitry 102 includes ANN 126 and ANN data store 128. In another embodiment, CT MAR circuitry 102 may further include detail image circuitry 122. In this embodiment, detail image circuitry 122 may be configured to receive input CT image data 132 from, e.g., CT scanner 104, and to provide detail CT image data 140 to ANN 126.

Processor circuitry 110 is configured to perform operations of CT MAR circuitry 102 including, for example, operations of projection completion circuitry 120, ANN 126 and/or detail image circuitry 122. Memory circuitry 112 may be configured to store information and/or data, e.g., input CT projection data 130, input CT image data 132, intermediate CT image data 138, detail CT image data 140 and/or CT output image data 142. ANN data store 128 may be included in memory circuitry 112. ANN data store 128 may contain one or more parameters associated with ANN 126.

Projection completion circuitry 120 is configured to receive input CT projection data 130 from, e.g., CT scanner 104. Input CT projection data 130 may include one or more sinograms output from CT scanner 104. The sinograms correspond to detected x-ray radiation that may be attenuated and/or scattered by at least a portion of object 106. If the object 106 contains a metal implant, at least some of the sinograms may be missing data, i.e., may include a metal trace. A corresponding CT image reconstructed based, at least in part, on such sinograms may include metal artifacts.

Projection completion circuitry 120 is configured to generate intermediate CT image data 138 based, at least in part, on the input CT projection data 130. Projection completion circuitry 120 may be configured to implement a projection completion technique. Projection completion techniques may include, but are not limited to, replacing corrupt sinogram data in a metal trace with data synthesized by an interpolation technique, reprojection from a prior image, and/or a combination of replacing and reprojection that may include normalization.

In one nonlimiting example, projection completion circuitry 120 may be configured to implement a normalized metal artifact reduction (NMAR) technique. The NMAR technique includes interpolation and normalization with prior CT projection data to replace data in the metal trace included in the input CT projection data 130. The NMAR technique includes segmenting metal artifacts in the image domain by thresholding. A three-dimensional forward projection may be configured to identify the metal trace in an original projection. Prior to interpolation, the projections may be normalized based on a three-dimensional forward projection of a prior image. The prior image may be obtained, for example, by a multi-threshold segmentation of the initial image. The original raw data are divided by the projection data of the prior image and, after interpolation, denormalized again.

In other words, in the NMAR technique, projection completion circuitry 120 is configured to obtain a metal image and a prior image that correspond to the input CT projection data 130 by thresholding. Projection completion circuitry 120 is configured to reconstruct the input sinogram to yield a corresponding uncorrected CT image. The uncorrected CT image may then be thresholded yielding a metal image and a prior image. Projection completion circuitry 120 is then configured to generate a sinogram corresponding to the metal image ("metal sinogram") and a sinogram corresponding to the prior image ("prior sinogram") by forward projection. The input sinogram may then be normalized by dividing it by the prior sinogram. Projection completion circuitry 120 may then be configured to utilize metal projections to determine where data in the normalized sinogram is replaced by interpolation. The interpolated and normalized sinogram may then be denormalized by multiplying it with the prior sinogram again to yield intermediate CT projection data. Projection completion circuitry 120 may then be configured to reconstruct intermediate CT image data 138 based, at least in part, on the intermediate CT projection data.

Thus, projection completion circuitry 120 may be configured to perform an initial correction via interpolation based, at least in part, on the input CT projection data 130 to yield the intermediate CT image data 138. A corresponding intermediate CT image generated based on the intermediate CT image data 138 is configured to have a reduced artifact compared to an uncorrected CT image reconstructed based, at least in part, on input CT projection data 130.

In an embodiment, ANN 126 is configured to receive intermediate CT image data 138 and to generate CT output image data 142 based, at least in part, on the intermediate CT image data 138. For example, ANN 126 may be configured to receive an intermediate image, I, and to provide as output an output image, Ỹ. The output image, Ỹ, is a function of the intermediate image, I, and characteristics of ANN 126.

In another embodiment, ANN 126 may be configured to receive intermediate CT image data 138 and detail CT image data 140. In this embodiment, ANN 126 is configured to generate CT output image data 142 based, at least in part, on the intermediate CT image data 138 and based, at least in part, on the detail CT image data 140. Detail image circuitry 122 may be configured to generate detail CT image data 140 based, at least in part, on input CT image data 132, as described herein.

ANN 126 may be trained prior to actual MAR operations on actual input CT projection data and/or actual input CT image data. Generally, training is supervised and includes providing training pairs that include input image and/or projection data and corresponding target output image data (i.e., ground truth). For each input image and/or projection data, parameters of ANN 126 may be adjusted to minimize a loss function. The loss function generally determines a difference between an output of ANN 126 for the training input and the target output image data.

In one nonlimiting example, the loss function is a mean squared error (MSE) loss function configured to calculate a pixel by pixel error between the ANN 126 actual output, Ỹ$_i$, and the target output, Y$_i$. The MSE loss function may be calculated as:

$$\mathcal{L}_{MSE} = \frac{1}{N}\sum_{i=1}^{N} \|\tilde{Y}_i - Y_i\|_F^2 \quad (1)$$

where N is the number of training samples and subscript i denotes the i-th sample in a training set.

In another nonlimiting example, the loss function may correspond to a perceptual loss function. For example, a perceptual loss function from a pre-trained VGG network may be used to optimize CT output image data 142 in a feature space to preserve texture as:

$$\mathcal{L}_P = \frac{1}{N}\sum_{i=1}^{N} \|\phi(\tilde{Y}_i) - \phi(Y_i)\|_F^2 \quad (2)$$

where φ is a feature extractor to indicate loss calculation in the feature space. An output of a selected convolution layer in the VGG network may be utilized as the feature extractor. In one nonlimiting example, the output of the 16$^{th}$ convolutional layer in the VGG network may be selected. However, this disclosure is not limited in this regard.

Thus, ANN 126 may be trained based, at least in part, on training data and based, at least in part, on a selected loss function.

Figure 2:
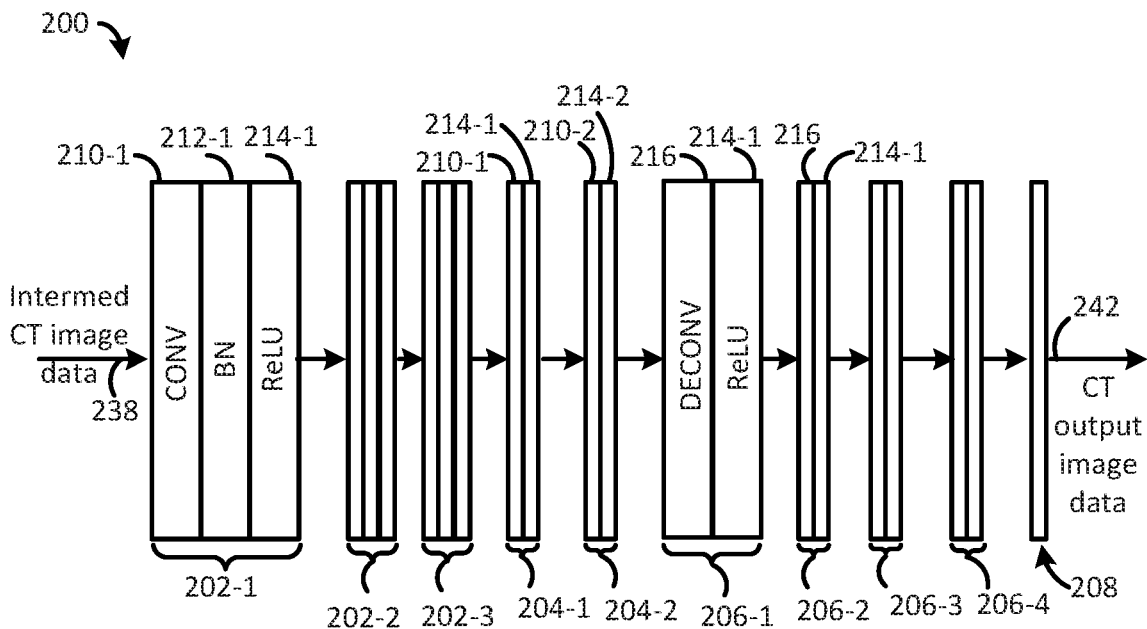
FIG. 2 illustrates a functional block diagram of a convolutional neural network (CNN) consistent with one embodiment of the present disclosure.

FIG. 2 illustrates a functional block diagram 200 of a convolutional neural network (CNN) consistent with one embodiment of the present disclosure. CNN 200 is one example of ANN 126 of FIG. 1. CNN 200 is configured to receive intermediate CT image data 238 as input and to provide CT output image data 242 as output. For example, the intermediate CT image data 238 may be received from projection completion circuitry, e.g., projection completion circuitry 120 of FIG. 1. The intermediate CT image data 238 and the CT output image data 242 may correspond to a portion (i.e., image patch) of a CT image.

CNN 200 includes a sequence of convolution stages 202-1, 202-2, 202-3, 204-1, 204-2, followed by a sequence of deconvolution stages 206-1, 206-2, 206-3, 206-4 followed by a final deconvolution layer 208. Convolution stages 202-1, 202-2, 202-3, e.g., first convolution stage 202-1, each include a convolution layer 210-1 followed by a batch normalization layer 212-1 followed by a rectified linear unit 214-1. The batch normalization 212-1 layer is configured to speed up the initial part of training. The rectified linear units 214-1 correspond to nonlinear activation functions. Convolution stage 204-1, includes a convolution layer 210-1 followed by a rectified linear unit 214-1. Convolution stage 204-2 includes a convolution layer 210-2 followed by a rectified linear unit 214-2. Deconvolution stages 206-1, 206-2, 206-3, 206-4, e.g., deconvolution stage 206-1, each include a deconvolution layer 216 followed by a rectified linear unit 214-1.

The first convolution stage 202-1 is configured to receive the intermediate CT image data 238 and the final deconvolution layer 208 is configured to provide as output the CT output image data 242. The convolution layers are configured to extract features from an input image patch, e.g., the intermediate CT image data 238, and map the features to a target image patch. The deconvolution layers are configured to use these features to build a predicted output, e.g., CT output image data 242.

In one nonlimiting example, convolution stages 202-1, 202-2, 202-3, 204-1 each have a 3×3 kernel and contain 32 filters. In this example, the input image patch (i.e., intermediate CT image data 238) and the output image patch (i.e., CT output image data 242) may both have size 32×32 pixels. Convolution stage 204-2 has a 3×3 kernel and contains 16 filters. The lesser number of filters of convolution stage 204-2 compared to the other convolution stages is configured to facilitate reconstruction of an output patch via the deconvolution stages using relatively more important features. Deconvolution stages 206-1, 206-2, 206-3, 206-4 each have a 3×3 kernel and contain 32 filters. Final convolution layer 208 has a 3×3 kernel and contains one filter. The final convolution layer 208 (i.e., the single filter) is configured to generate one feature map as the output.

Turning again to FIG. 1, it may be appreciated that intermediate CT image data 138 output from the projection completion circuitry 120 may contain relatively more content information and relatively fewer streaks (i.e., metal artifacts) while the input CT image data 132 (i.e., uncorrected CT image data) may contain relatively more streaks and relatively less content. To harness the content information included in the intermediate CT image data 138 and the streak information included in input CT image data 132, both the intermediate CT image data 138 and detail CT image data 140 generated based, at least in part, on the input CT image data 132, may be provided to ANN 126.

Detail image circuitry 122 is configured to generate a detail image, D, by passing an uncorrected input CT image (e.g., input CT image data 132), U, through a low-pass guided filter. The filtered image (i.e., base image), $\mathcal{F}$(U), may then be subtracted from the uncorrected input CT image as:

$$D = U - \mathcal{F}(U) \quad (3)$$

to yield the detail image, D, and corresponding detail CT image data 140. After subtracting the base image from the uncorrected input CT image, background interference is removed and metal streaks and/or object structures may remain in the detail image. The detail image is configured to facilitate learning by identifying prominent streaks in an uncorrected image.

ANN 126 may then be configured to receive an intermediate image, I, and the detail image, D, and to provide as output an output image, Ŷ. The output image, Ŷ, is a function of the intermediate image, I, and the detail image, D.

Figure 3:
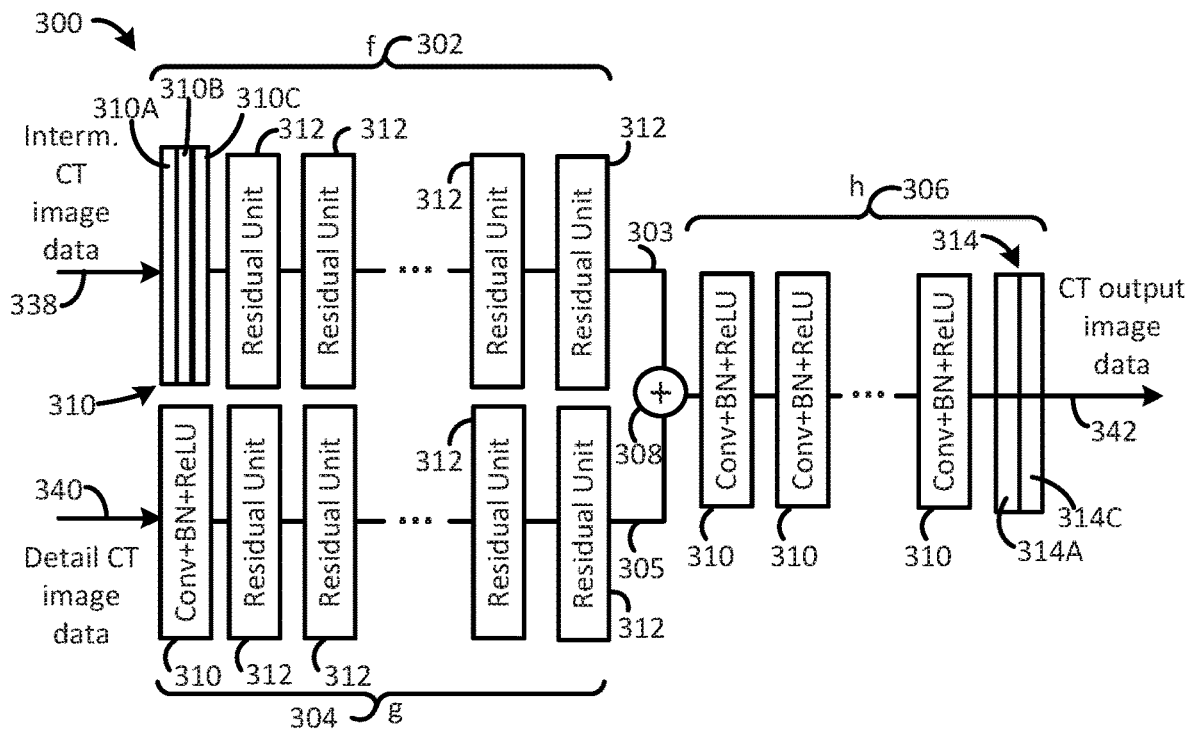
FIG. 3 illustrates a functional block diagram of another CNN consistent with several embodiments of the present disclosure.

FIG. 3 illustrates a functional block diagram 300 of another CNN consistent with several embodiments of the present disclosure. CNN 300 is an example of ANN 126 of FIG. 1. CNN 300 is configured to receive intermediate CT image data 338 and detail CT image data 340 as input and to provide CT output image data 342 as output. The intermediate CT image data 338, detail CT image data 340 and the CT output image data 342 may correspond to a portion (i.e., image patch) of a CT image. The intermediate CT image data 338 may correspond to intermediate CT image data 138, detail CT image data 340 may correspond to detail CT image data 140 as input and CT output image data 342 may correspond to CT output image data 142 of FIG. 1.

CNN 300 includes an intermediate stream ("f") 302, a detail stream ("g") 304, a combiner stage 308 and an output stream ("h") 306. The intermediate stream 302 is configured to be in parallel with the detail stream 304. The intermediate stream 302 is configured to receive the intermediate CT image data 338 and the detail stream 304 is configured to receive the detail CT image data 340. An output 303 of the intermediate stream 302 and an output 305 of the detail stream 304 are each coupled to the combiner stage 308. Output 303 and output 305 correspond to feature maps of their respective stream f 302 and g 304. An output of the combiner stage 308 is coupled to an input of the output stream h 306. In one nonlimiting example the combiner stage 308 corresponds to a summing junction. In one nonlimiting example, the output of CNN may be expressed as:

$$\tilde{Y} = h(f(I) + g(D)) \quad (5)$$

where I corresponds to intermediate CT image data 338, D corresponds to detail CT image data 340 and Ŷ corresponds to CT output image data 342.

The intermediate stream 302 and the detail stream 304 each include an initial convolution stage, e.g., convolution stage 310, coupled to their respective input followed by a sequence of residual units, e.g., residual unit 312. The output stream 306 includes a sequence of convolution stages, e.g., convolution stage 310, followed by an output stage 314. Thus, the initial convolution stage 310 of intermediate stream 302 is configured to receive intermediate CT image data 338 and the initial convolution stage 310 of the detail stream 304 is configured to receive the detail CT image data 340. Each convolution stage 310 includes a convolution layer 310A followed by a batch normalization layer 310B followed by a rectified linear unit 310C. The output stage 314 includes a convolution layer 314A followed by a rectified linear unit 314C.

In one nonlimiting example, the intermediate stream 302 and the detail stream 304 may each include a sequence of 20 residual units following their respective initial convolution stage. Continuing with this example, the output stream 306 may include a sequence of eight convolution stages 310 followed by the output stage 314. Each convolution stage may include 32 filters and the output stage 314 includes one filter. Each convolution stage 310 and the output stage have a 3×3 kernel and use zero padding. For this example, the input patches and output patch (i.e., intermediate CT image data 338, detail CT image data 340 and CT output image data 342) each have size 56×56 pixels.

Figure 4:
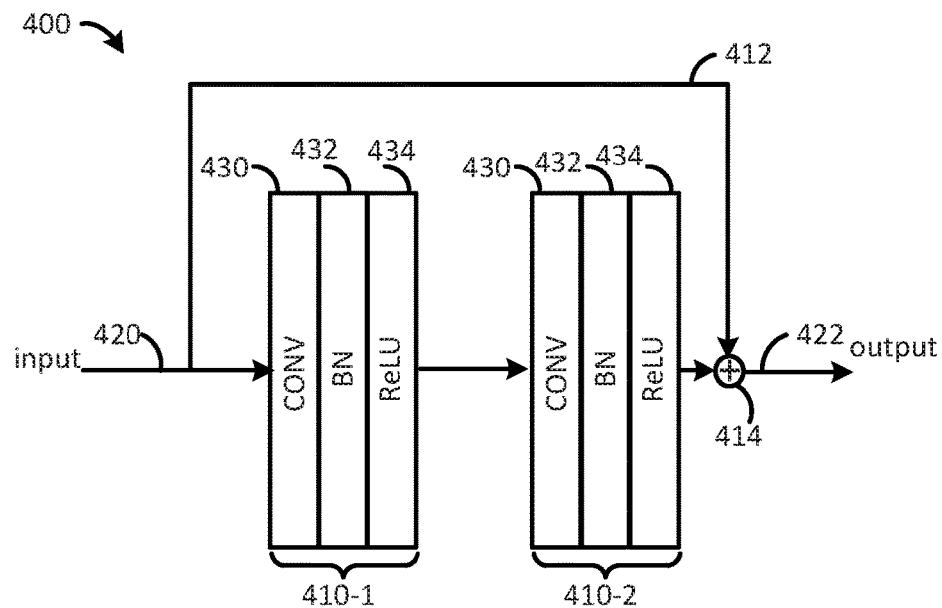
FIG. 4 illustrates a functional block diagram of a residual unit of the CNN of FIG. 3 consistent with several embodiments of the present disclosure.

FIG. 4 illustrates a functional block diagram 400 of a residual unit of the CNN 300 of FIG. 3 consistent with several embodiments of the present disclosure. Residual unit 400 is one example of residual unit 312 of FIG. 3. Residual unit 400 is configured to receive an input 420 and to provide an output 422. Residual unit 400 includes a sequence of two convolution stages 410-1, 410-2. Residual unit 400 further includes a combiner stage 414, e.g., a summing junction. Each convolution stage 410-1, 410-2 includes a convolution layer 430 followed by a batch normalization layer 432 followed by a rectified linear unit 434 activation function to maintain nonlinearity. The input 420 is coupled to the convolution layer 430 of the first convolution stage 410-1 and to the combiner stage 414. An output of the rectified linear unit 434 of the second convolution stage 410-2 is also coupled to the combiner stage 414. An output of the combiner stage 414 corresponds to output 422.

During training, within each residual unit 312, e.g., residual unit 400, the CNN 300 is configured to learn a residual error between the input, e.g., input 420, and the output, e.g., output 422, of the residual unit 400. Training on the residual differences may reduce a mapping range of pixel values used for learning. The residual units are configured to reduce a solution range and, thus, facilitate learning.

Figure 5:
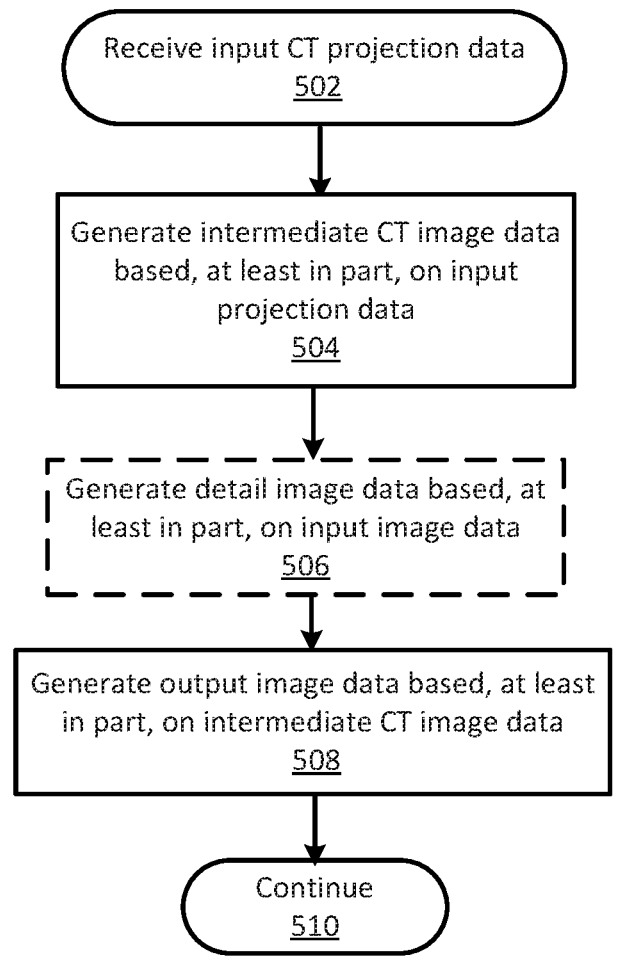
FIG. 5 is a flowchart of example CT metal artifact reduction operations consistent with several embodiments of the present disclosure.

FIG. 5 is a flowchart 500 of example CT metal artifact reduction operations consistent with several embodiments of the present disclosure. In particular, flowchart 500 illustrates generating CT output image data based, at least in part, on input CT projection data. The CT output image is configured to contain relatively fewer artifacts than an uncorrected CT image reconstructed from the input CT projection data. The operations of flowchart 500 may be performed by, for example, CT MAR circuitry 102 (e.g., projection completion circuitry 120, ANN 126 and/or detail image circuitry 122) of FIG. 1. The operations of flowchart 500 may be performed during training and/or during operation of CT MAR circuitry. During training, operations may further include comparing the generated CT output image data to ground truth artifact-free images (i.e., training images) and adjusting ANN parameters based, at least in part, on a loss function.

In some embodiments, operations of flowchart 500 may begin with receiving input CT projection data at operation 502. For example, the CT projection data may be received from a CT scanner. Intermediate CT image data may be generated based, at least in part, on input CT projection data at operation 504. In some embodiments, detail CT image data may be generated at operation 506. CT output image data may be generated based, at least in part, on the intermediate CT image data at operation 508. The CT output image data may be generated by an ANN. In some embodiments, the CT output image data may be generated further based, at least in part, on detail CT image data. Program flow may then continue at operation 510.

Thus, output CT image data, that includes relatively fewer artifacts than uncorrected input CT image data may be generated based, at least in part, on input CT projection data.

EXAMPLES

Figure 7:
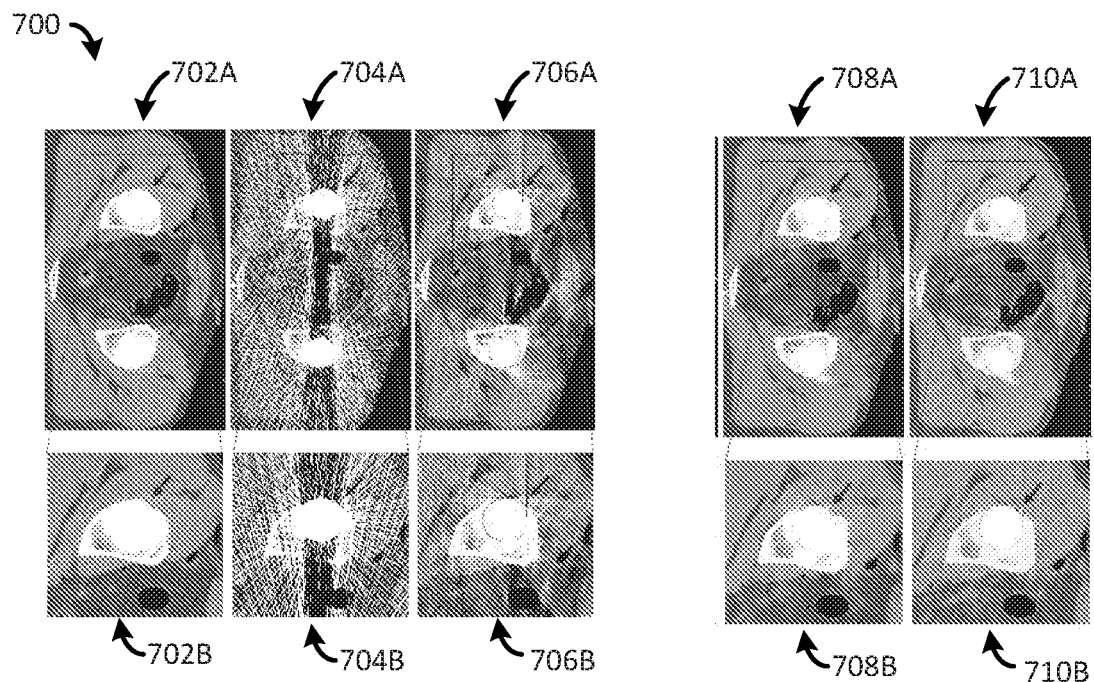
FIG. 7 illustrates hip prosthesis images for the example CNN of FIG. 3.
Figure 8:
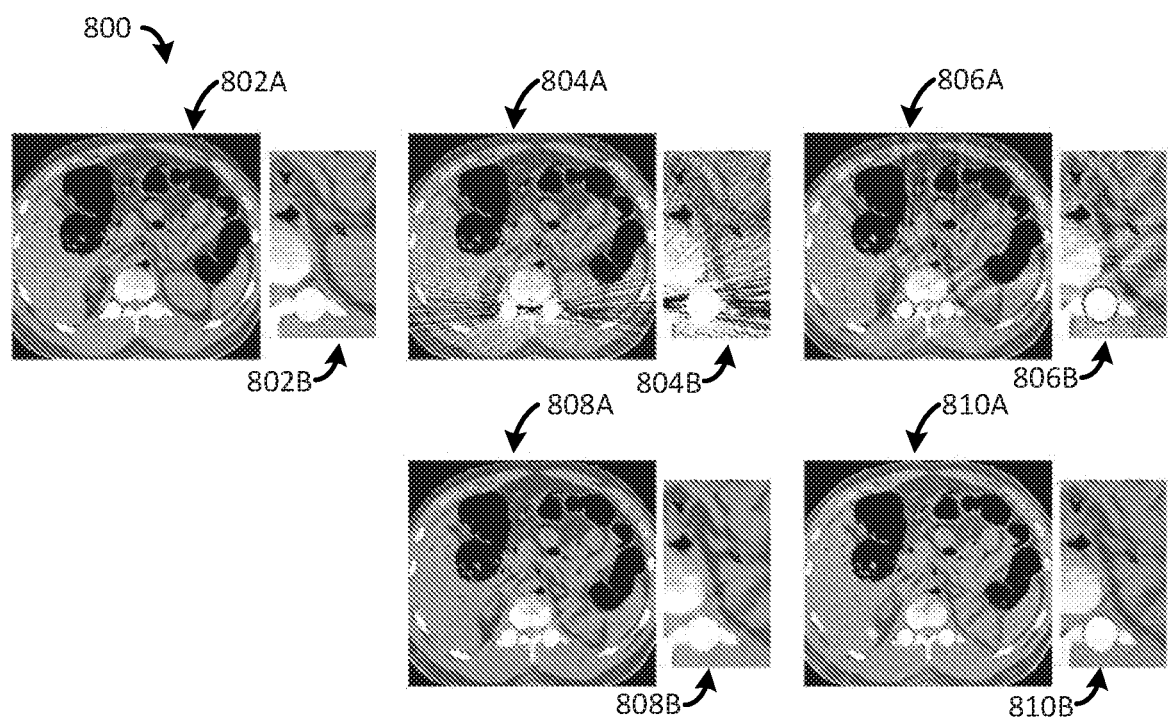
FIG. 8 illustrates spinal fixation rod images for the example CNN of FIG. 3.

FIGS. 6A through 6D illustrate plots of loss versus epoch for one example of the CNN of FIG. 3. FIG. 7 illustrates hip prosthesis images for the example CNN 300 of FIG. 3. FIG. 8 illustrates spinal fixation rod images for the example CNN 300 of FIG. 3. In FIG. 7 and FIG. 8, reference designators ending in letter B correspond to a magnified portion of a corresponding reference designator ending in letter A.

The Visible Human Project dataset was used as the basis for all training and validation data for CNN 300. Two sets of voxelized phantoms were created from the volumetric data in the pelvic and spinal regions. Titanium was added in the femoral head region to represent a hip prosthesis (up to 20 mm radius) and next to vertebrae to represent spinal fixation rods (up to 10 mm radius). Then, a CT simulation technique called CatSim (General Electric Global Research Center, Niskayuna, N.Y.) was used to scan both sets of phantoms to generate the metal corrupted and artifact-free projections, and reconstruction was performed with filtered back-projection. The scan geometry simulated a GE LightSpeed VCT system architecture, with parameters including a tube voltage of 120 kVp, a tube current of 300 mA, 108 photons, 888 detector columns, and 720 views at uniform projection angles between 0-360 degrees. The phantoms without metal were scanned with a 100 keV monoenergetic beam to minimize general noise and beam hardening artifacts.

The 512×512 reconstructed images of the metal-added phantoms contained relatively severe artifacts. An intermediate CT image was reconstructed based, at least in part, on input projection CT data by projection completion circuitry 120 configured to implement the NMAR technique, as described herein. The intermediate CT image served as the input to the intermediate stream 302 of the CNN 300 of FIG. 3. Scans on the datasets without metal yielded images without artifacts to serve as the "ground truth" and target/label of the CNN. The phantom pairs were scanned for a total of 50 image slices at 1 mm thickness. Eight images were reserved for testing/validation and not used in the training process. From the full-size images, approximately 150,000 patches of size 56×56 were extracted from the images to form the dataset to train the CNNs.

Figure 6A:
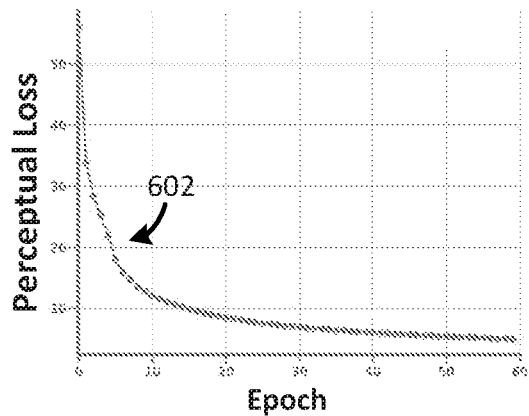
FIGS. 6A through 6D illustrate plots of loss versus epoch for one example of the CNN of FIG. 3.
Figure 6B:
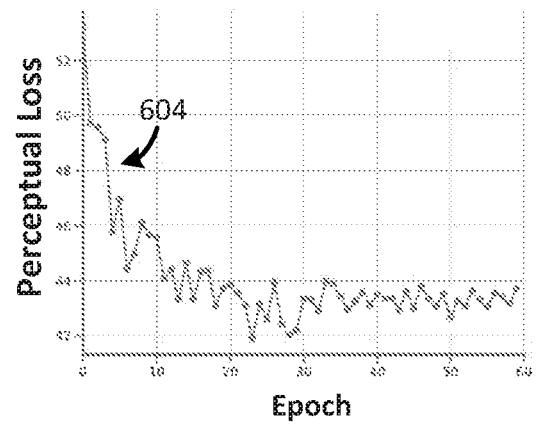
Figure 6C:
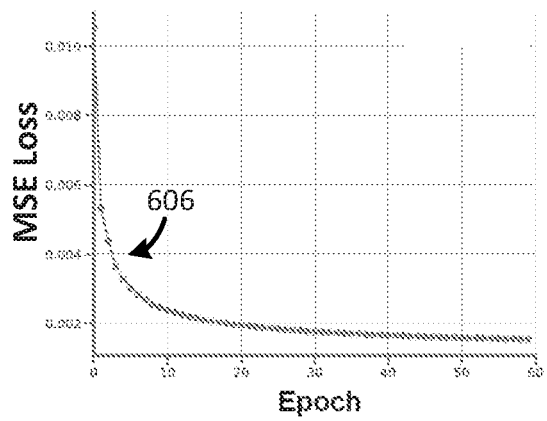
Figure 6D:
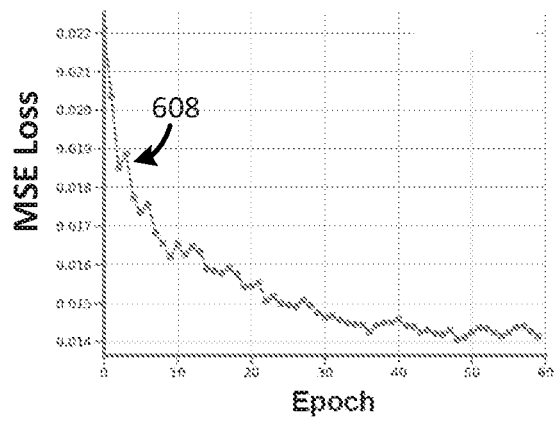

Turning now to FIGS. 6A through 6D, FIG. 6A illustrates a plot 602 of perceptual loss versus epoch for training operations, FIG. 6B illustrates a plot 604 of perceptual loss versus epoch for testing (i.e., post-training) operations, FIG. 6C illustrates a plot 606 of MSE loss versus epoch for training operations and FIG. 6C illustrates a plot 608 of MSE loss versus epoch for testing operations. During training, parameter weights in each layer of the CNN 300 were adjusted to minimize a loss function (e.g., perceptual or MSE). Training was run on an Nvidia GeForce GTX 1080 Ti graphics card using the TensorFlow framework in Python for 60 epochs. The network learning rate α was initialized to $10^{-3}$. In the t-th training epoch, the learning rate $α_t$ was decayed proportional to the epoch number: $α_t = α/\sqrt{t}$. The training process converged within 60 epochs, as indicated by loss curves 602, 604, 606, 608 of FIGS. 6A through 6D, respectively.

Turning now to FIG. 7 and FIG. 8, images 702A, 702B are artifact-free reference CT images (i.e., "ground truth"). Images 704A, 704B are uncorrected input CT images. Images 706A, 706B are intermediate CT images output from projection completion circuitry. Images 708A, 708B are CT output images of a CT MAR device for CNN 300 trained with an MSE loss function. Images 710A, 710B are CT output images for CNN 300 trained with a perceptual loss function. Images 802A, 802B are artifact-free reference CT images (i.e., "ground truth"). Images 804A, 804B are uncorrected input CT images. Images 806A, 806B are intermediate CT images output from projection completion circuitry. Images 808A, 808B are CT output images of a CT MAR device for CNN 300 trained with an MSE loss function. Images 810A, 810B are CT output images for CNN 300 trained with a perceptual loss function.

To validate the network performances, hip (FIG. 7) and spine (FIG. 8) image slices withheld from training were used. The uncorrected CT images 704A, 704B, 804A, 804B, reconstructed from raw projection data, illustrate a poor image with many streaks, a dark band along the lines of greatest attenuation, and regions of missing data. The pre-correction artifacts are severe in the hip case due to the large implant size. The output images 708A, 708B, 808A, 808B illustrate relatively fewer streak artifacts compared to intermediate the images 706A, 706B, 806A, 806B.

Thus, a method and/or apparatus are configured to perform an initial metal artifact reduction using a projection completion technique. Projection completion may be performed on input CT projection data to produce intermediate CT image data. The method and/or apparatus are configured to perform further metal artifact reduction on the intermediate CT image data using an artificial neural network. The combination of projection completion and ANN MAR is configured to provide relatively better MAR than either technique alone.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hardwired circuitry, programmable circuitry such as computer processors including one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Processor circuitry 110 may include, but is not limited to, a single core processing unit, a multicore processor, a graphics processing unit (GPU), a plurality of GPUs operating in parallel, a microcontroller, an application-specific integrated circuit (ASIC), a field programmable gate array (FPGA), a programmable logic device (PLD), etc.

Memory circuitry 112 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively memory circuitry 112 may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

What is claimed is:

1. A method for computed tomography (CT) metal artifact reduction (MAR), the method comprising:
   generating, by a projection completion circuitry, an intermediate CT image data based, at least in part, on input CT projection data, the intermediate CT image data configured to include-fewer artifacts than an uncorrected CT image reconstructed from the input CT projection data, wherein generating the intermediate CT image data comprises interpolation and normalization with prior CT projection data;
   generating, by detail image circuitry, detail CT image data based, at least in part, on input CT image data; and
   generating, by an artificial neural network (ANN), CT output image data based, at least in part, on the intermediate CT image data and the detail CT image data, the CT output image data configured to include fewer artifacts compared to the intermediate CT image data, the ANN comprising an intermediate CT image data stream, a detail CT image data stream, and a CT output image data stream, the intermediate CT image data stream and the detail CT image data stream each comprising an initial convolution stage and a sequence of residual units, the CT output image data stream comprising a sequence of convolution stages and an output stage, each convolution stage comprising a convolution layer, a batch normalization layer, and a rectified linear unit, and the output stage comprising a convolution layer and a rectified linear unit.

2. The method of claim 1, wherein the ANN is trained based, at least in part, on a mean squared error loss function.

3. The method of claim 1, wherein the ANN is trained based, at least in part, on a perceptual loss function.

4. The method of claim 1, wherein the ANN is a convolutional neural network (CNN).

5. The method of claim 1, wherein each residual unit comprises a sequence of a first convolution stage, a second convolution stage and a combiner stage, the combiner stage configured to receive an input to the residual unit and an output of the second convolution stage, an output of the residual unit corresponding to an output of the combiner stage.

6. An apparatus for computed tomography (CT) metal artifact reduction (MAR), the apparatus comprising:

a projection completion circuitry configured to generate an intermediate CT image data based, at least in part, on input CT projection data, the intermediate CT image data configured to include fewer artifacts than an uncorrected CT image reconstructed from the input CT projection data, wherein generating the intermediate CT image data comprises interpolation and normalization with prior CT projection data;
   detail image circuitry configured to generate detail CT image data based, at least in part, on input CT image data; and
   an artificial neural network (ANN) configured to generate CT output image data based, at least in part, on the intermediate CT image data and the detail CT image data, the CT output image data configured to include fewer artifacts compared to the intermediate CT image data, the ANN comprising an intermediate CT image data stream, a detail CT image data stream, and a CT output image data stream, the intermediate CT image data stream and the detail CT image data stream each comprising an initial convolution stage and a sequence of residual units, the CT output image data stream comprising a sequence of convolution stages and an output stage, each convolution stage comprising a convolution layer, a batch normalization layer, and a rectified linear unit, and the output stage comprising a convolution layer and a rectified linear unit.

7. The apparatus of claim 6, wherein the ANN is trained based, at least in part, on a mean squared error loss function.

8. The apparatus of claim 6, wherein the ANN is trained based, at least in part, on a perceptual loss function.

9. The apparatus of claim 6, wherein the ANN is a convolutional neural network (CNN).

10. The apparatus of claim 6, wherein each residual unit comprises a sequence of a first convolution stage, a second convolution stage and a combiner stage, the combiner stage configured to receive an input to the residual unit and an output of the second convolution stage, an output of the residual unit corresponding to an output of the combiner stage.

11. A computed tomography (CT) metal artifact reduction (MAR) device comprising means to perform the method of claim 1.

12. A computer readable storage device having stored thereon instructions that when executed by one or more processors result in the following operations comprising the method according to claim 1.

* * * * *